(12) United States Patent
Waksmundzki et al.

(10) Patent No.: US 6,838,591 B2
(45) Date of Patent: Jan. 4, 2005

(54) ABSORBENT ARTICLE WITH C-FOLD LAYER FLUID ACQUISITION SYSTEM, C-FOLD LAYER FLUID ACQUISITION SYSTEM FOR USE IN ABSORBENT ARTICLES AND METHOD OF MAKING THE SAME

(75) Inventors: Andrew Waksmundzki, Jackson, NJ (US); Kim Babusik, Wenonah, NJ (US); Joan Rodgers, Brookhaven, PA (US)

(73) Assignee: Tyco Healthcare Retail Services, AG (CH)

( * ) Notice: Subject to any disclaimer, the term of this patent is extended or adjusted under 35 U.S.C. 154(b) by 304 days.

(21) Appl. No.: 10/139,556

(22) Filed: May 6, 2002

(65) Prior Publication Data

US 2003/0208176 A1 Nov. 6, 2003

(51) Int. Cl.[7] ............................................... A61F 13/15
(52) U.S. Cl. ...................................... 604/382; 604/378
(58) Field of Search ......................... 604/385.201, 382, 604/367, 378, 381, 383

(56) References Cited

U.S. PATENT DOCUMENTS

| | | | |
|---|---|---|---|
| 3,968,798 A | 7/1976 | Hokanson | |
| 4,615,696 A * | 10/1986 | Jackson et al. | 604/389 |
| 4,695,278 A | 9/1987 | Lawson | |
| 4,795,454 A | 1/1989 | Dragoo | |
| 4,960,477 A * | 10/1990 | Mesek | 156/209 |
| 4,988,344 A | 1/1991 | Reising et al. | |
| 4,994,037 A | 2/1991 | Bernardin | |
| 5,294,478 A | 3/1994 | Wanek et al. | |
| 5,300,054 A | 4/1994 | Feist et al. | |
| 5,304,161 A | 4/1994 | Noel et al. | |
| 5,387,208 A | 2/1995 | Ashton et al. | |
| 5,460,622 A | 10/1995 | Dragoo et al. | |
| 5,486,167 A | 1/1996 | Dragoo et al. | |
| 5,520,673 A | 5/1996 | Yarbrough et al. | |
| 5,522,809 A | 6/1996 | Larsonneur | |
| 5,558,655 A | 9/1996 | Jezzi et al. | |
| 5,591,149 A | 1/1997 | Cree et al. | |
| 5,607,414 A | 3/1997 | Richards et al. | |
| 5,609,588 A | 3/1997 | DiPalma et al. | |
| 5,730,737 A | 3/1998 | Widlund et al. | |
| 5,752,945 A | 5/1998 | Mosley et al. | |
| 5,762,642 A | 6/1998 | Coles et al. | |
| 5,833,678 A | 11/1998 | Ashton et al. | |
| 5,843,055 A | 12/1998 | Seger | |
| 5,855,572 A | 1/1999 | Schmidt | |
| 5,895,379 A | 4/1999 | Litchholt et al. | |
| 5,906,602 A | 5/1999 | Weber et al. | |
| 6,066,775 A | 5/2000 | Bachar | |
| 6,103,953 A | 8/2000 | Cree et al. | |
| 2003/0113507 A1 * | 6/2003 | Niemeyer et al. | 428/77 |
| 2003/0135177 A1 * | 7/2003 | Baker | 604/368 |

* cited by examiner

*Primary Examiner*—Larry I. Schwartz
*Assistant Examiner*—C. Lynne Anderson
(74) *Attorney, Agent, or Firm*—Caesar, Rivise, Bernstein, Cohen & Pokotilow, Ltd.

(57) ABSTRACT

A disposable absorbent article, e.g., a diaper, having a top sheet, a back sheet, a core and a fluid acquisition system. The fluid acquisition system is formed by wrapping a layer of a non-woven material about the core, so that the marginal edge portions of the layer overlap each other over the upper surface of the core. The overlapping marginal edge portions are hydrophillic to form a dual layer fluid acquisition system. The remainder of the layer of non-woven material is hydrophobic. An additional layer can be located adjacent the overlapping portions to form a three layer acquisition system.

59 Claims, 6 Drawing Sheets

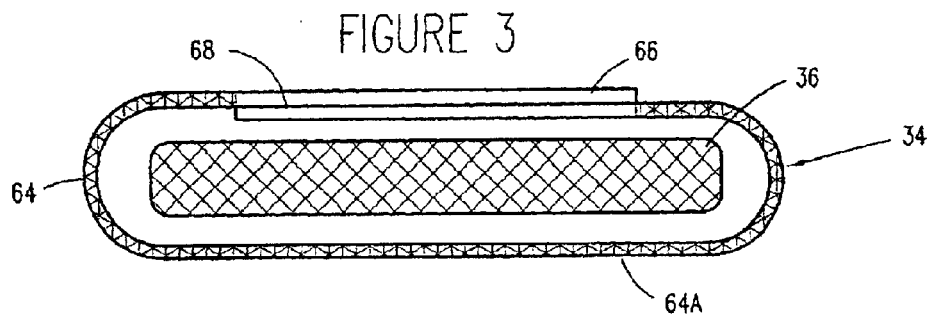
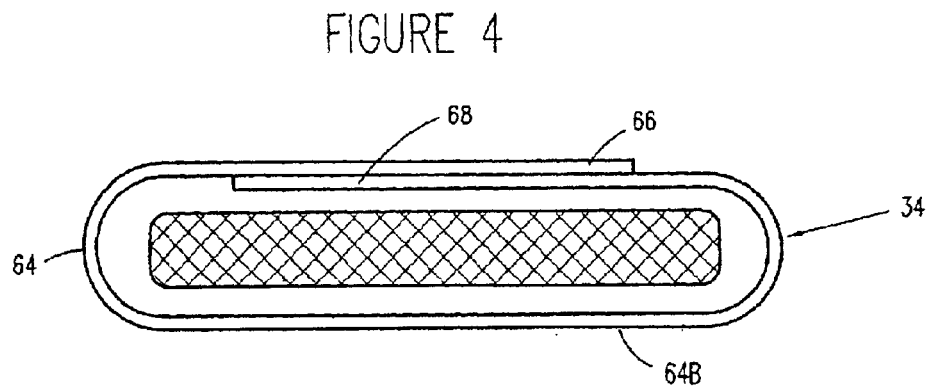
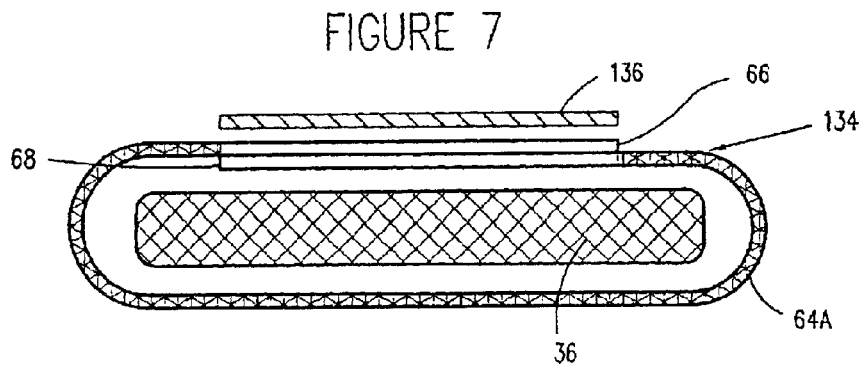
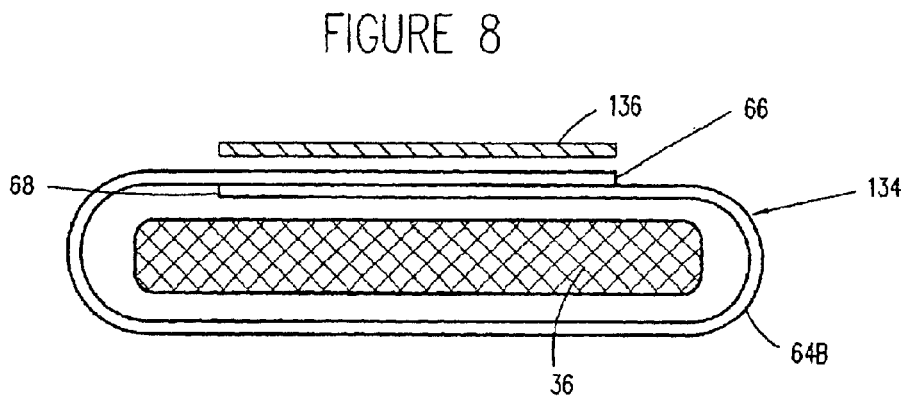

ABSORBENT ARTICLE WITH C-FOLD LAYER FLUID ACQUISITION SYSTEM, C-FOLD LAYER FLUID ACQUISITION SYSTEM FOR USE IN ABSORBENT ARTICLES AND METHOD OF MAKING THE SAME

FIELD OF THE INVENTION

This invention relates generally to disposable absorbent articles and more specifically to disposable absorbent articles, e.g., diapers, which exhibit enhanced liquid absorption and trapping characteristics and which are easy to manufacture.

BACKGROUND OF THE INVENTION

Disposable absorbent articles, e.g., diapers, catamenial pads, panty liners, shields, etc., frequently make use of a liquid absorbent core located between a top sheet and a back sheet. The top sheet is commonly formed of a material which is pervious to body fluids, e.g., urine, to promote the transfer of such fluids into the core with minimal fluid retention by the top sheet. The back-sheet is commonly formed of a liquid impervious or hydrophobic material to form a barrier wall so that any fluid absorbed by the article cannot escape out the back-sheet. In many cases, a fluid "acquisition," "surge" or "transfer" layer is located between the top sheet and the core to facilitate the transference of body fluid(s) into the core.

In co-pending U.S. patent application Ser. No. 09/439,793, filed on Nov. 12, 1999, entitled Absorbent Article with Improved Fluid Acquisition System, which is assigned to the same assignee as this invention, namely, Tyco Healthcare Retail Group, Inc., there is disclosed an absorbent article, e.g., a diaper, arranged to be worn by a wearer to trap and collect fluid waste products, e.g., urine, of the wearer. The article has a flexible chassis and plural tabs for holding the diaper in place on the wearer. The chassis is made up of a top sheet, a fluid acquisition system, and a fluid absorbent core. The top sheet is formed of a fluid pervious material, e.g., a fibrous material. The core includes fast acting fluid absorbing material, e.g., fluff, and a slow acting fluid absorbing and retaining material, e.g., SAP. The fluid acquisition system comprises a first fluid acquisition layer formed of apertured polymeric, e.g., three dimensional, film and a second fluid acquisition layer, e.g., a fibrous material, secured together and located between the top sheet and the core, with the first fluid acquisition layer facing the top sheet and the second fluid acquisition layer facing the core. The fluid acquisition system serves to facilitate the transference of fluid into the core, e.g., spread out the fluid over the core and providing it to the core at a rate at which the materials of the core can accommodate.

In another co-pending U.S. patent application Ser. No. 09/562,541, filed on May 2, 2000, entitled Absorbent Article with Improved Fluid Acquisition System And Method Of Making The Same, which is a Continuation-In-Part of Ser. No. 09/439,793, filed on Nov. 12, 1999 and is also assigned to the same assignee as this invention, there is disclosed an absorbent article with a dual layer fluid acquisition system. That application discloses a disposable absorbent article, e.g., a diaper, and a method of making it. The article has a flexible chassis and plural tabs for holding the diaper in place on the wearer. The chassis is made up of a top sheet, a fluid acquisition system, and a fluid absorbent core. The top sheet is formed of a fluid pervious material, e.g., a fibrous material. The core includes fast acting fluid absorbing material, e.g., fluff, and a slow acting fluid absorbing and retaining material, e.g., SAP. The fluid acquisition system comprises a first fluid acquisition layer formed of apertured polymeric, e.g., three dimensional film, and a second fluid acquisition layer, e.g., a fibrous material, secured together and located between the top sheet and the core, with the first fluid acquisition layer facing the top sheet and the second fluid acquisition layer facing the core. The fluid acquisition system serves to facilitate the transference of fluid into the core, e.g., spread out the fluid over the core and providing it to the core at a rate at which the materials of the core can accommodate. The first and second acquisition layers may be joined or bonded together via various techniques, such as by adhesives, ultrasonic bonding, heat sealing, hot knife-slitting, hydroentanglement, physical stitching or sewing, etc.

The patent literature includes other patents relating to absorbent articles with fluid acquisition systems. For example, U.S. Pat. No. 5,300,054 (Feist et al.) is directed to an absorbent article, such as a diaper, which has a rapid acquiring wrapped multiple layer absorbent body in an absorbent core. The absorbent article includes a liquid pervious top sheet, a liquid impervious back sheet, and an absorbent core position between the top sheet and the back sheet. The absorbent core comprises a multiple layer absorbent body having an acquisition layer. A fluid transporting wrapping at least partially surrounds the multiple layer absorbent body to form a wrapped multiple layer absorbent body. See FIG. 9. As shown in this cross-section, the multiple layer absorbent core is wrapped in a low density wrapping of material that is capable of transporting fluids. The wrapped multiple layer absorbent body overlies a storage layer material, such as a layer of air-felt. The high-loft wrapping of material serves as an additional acquisition/distribution layer to transport exudates to the layer of air-felt. The double layer of the wrapping is located above the air-felt storage layer, i.e., the wrapping does not surround the storage layer over which the double layer resides.

U.S. Pat. No. 5,752,945 (Mosley et al.) discloses an absorbent article, such as a diaper, that has an absorbing core and an outer porous cover sheet to allow transfer of liquids through the cover sheet and into the core. A liquid transfer sheet, in the form of a non-woven fabric, is located between the cover sheet and the core. The transfer sheet has at least two layers, with the layer facing the cover sheet having relatively coarse fibers and the layer facing the core having relatively fine fibers. This arrangement allows for more efficient transfer of liquids into the core, while minimizing wetback.

U.S. Pat. No. 5,762,642 (Coles, et al.) discloses an absorbent article having a liquid pervious top sheet, a liquid impervious back sheet and an absorbent core interposed between the top sheet and the back sheet. As can be seen in FIGS. 4A and 4B, the core is wrapped with folded tissue which overlap each other. The overlapped portion is on the back sheet side of the article.

U.S. Pat. No. 6,066,775 (Bachar) is directed to a method of manufacturing an absorbent core for a diaper. Here, a non-woven sheet is provided which includes three coextensive longitudinal trisections, a center trisection, and two outer trisections. The non-woven sheet further includes three coextensive latitudinal trisections. A super-absorbent polymer is applied to two of the latitudinal trisections. The two outer longitudinal trisections are folded over the super-absorbent polymer in a triple fold so as to form a sandwiched absorbent core including a bottom layer of the woven sheet, layer of the super absorbent polymer, and two upper layers of the non-woven sheet. The desired goal of this invention is to place 95% of the total super absorbent polymer in the front and crotch portions and 5% in the rear portion of the article.

U.S. Pat. No. 6,103,953 (Cree, et al.) is directed to an absorbent article, such as a diaper, having fused layers. The article includes a liquid pervious apertured film top sheet, a liquid impervious back sheet, an absorbent core, and a woven or unwoven acquisition layer. The acquisition layer may be a double, z-folded sheet.

U.S. Pat. No. 3,968,798 (Hokanson) discloses a disposable incontinent pad, such as a diaper, which includes a fluid absorbent matrix with a facing sheet, and a water impervious backing sheet having the matrix therebetween. The article has a C-fold configuration with the backing sheet overlapping the fold lines onto the facing sheets such that, when the pad is worn, it is resistant to lateral run-off of body fluid.

Other examples of prior art acquisition layers are disclosed in U.S. Pat. No. 4,988,344 (Reising et al.), U.S. Pat. No. 4,994,037 (Bernardin), U.S. Pat. No. 5,294,478 (Wanek et al.), U.S. Pat. No. 5,300,054 (Feist et al.), U.S. Pat. No. 5,304,161 (Noel et al.), U.S. Pat. No. 5,387,208 (Ashton et al.), U.S. Pat. No. 5,460,622 (Dragoo et al.), U.S. Pat. No. 5,486,167 (Dragoo et al.), U.S. Pat. No. 5,520,673 (Yarbrough et al.), U.S. Pat. No. 5,522,809 (Larsonneur), U.S. Pat. No. 5,558,655 (Jezzi et al.), U.S. Pat. No. 5,591,149 (Cree et al.), U.S. Pat. No. 5,607,414 (Richards et al.), U.S. Pat. No. 5,609,588 (DiPalma et al.), U.S. Pat. No. 5,730,737 (Widlund et al.), U.S. Pat. No. 5,752,945 (Mosley et al.), U.S. Pat. No. 5,833,678 (Ashton et al.), U.S. Pat. No. 5,843,055 (Seger), U.S. Pat. No. 5,855,572 (Schmidt), U.S. Pat. No. 5,895,379 (Litchholt et al.), and U.S. Pat. No. 5,906,602 (Weber et al.).

Examples of commercially available materials used for acquisition layers in disposable absorbent articles are through-air bond staple fibers, adhesively bonded staple fibers, and thermally point bonded staple fibers. Moreover, various absorbent articles which are commercially available have made use of various layers of materials, some of which make up an acquisition system. For example, sanitary pads made by Tyco Healthcare Retail Group, Inc. and sold under the trademark EVERYDAY PANTILINER have included a top sheet formed of a fibrous material over the marginal edges of the pad, but not over the intake or "target" zone (i.e., the area at which the body fluid(s) gain(s) ingress into the absorbent article), a three dimensional apertured film forming the top layer of the intake/target zone, a fluid acquisition layer formed of a fibrous material (non-woven) web, and a core formed of an air laid web containing super absorbent material. Other pads in the form of Ultra Thins are also made by Tyco Healthcare Retail Group, Inc. and sold under trademark FRESH TIMES have included a top sheet formed of an apertured film, an air-laid acquisition layer and a core formed of a combination of air-laid and SAP or an air laid super absorbent material. Still other pads in the form of Contour Maxi pads are made by Tyco Healthcare, Inc. and sold under the trademark FRESH TIMES have included a top sheet formed of an apertured film and a core formed fluff. Still other pads in the form of Maxi pads are made by Tyco Healthcare Retail Group, Inc. and sold under the trademark FRESH TIMES have included a top sheet formed of a fibrous material, a tissue fluid acquisition layer and a core formed of fluff. Diapers made by Tyco Healthcare Retail Group, Inc. and sold under the trademark HAPPIES have included a non-woven top sheet, a through-air-bonded (or non-woven) acquisition layer, a tissue layer, and an absorbent core made of fluff and SAP.

While the aforementioned absorbent articles and/or fluid acquisition systems are suitable for their intended purposes, they still leave something to be desired from the standpoints of simplicity of construction and ease and economy of manufacture.

SUMMARY OF THE INVENTION

This invention includes a disposable absorbent article, e.g., a diaper, arranged to be worn by a wearer to trap and collect fluid waste products of the wearer, a fluid acquisition system used in the absorbent article and a method of making the fluid acquisition system and absorbent article.

The absorbent article has a top sheet, the fluid acquisition system, a fluid absorbent core, and a back sheet. The top sheet is disposed over the core. The core has a top surface located adjacent the top sheet and a bottom surface located adjacent the back sheet.

The fluid acquisition system comprises a layer of a non-woven material wrapped about the core and having a pair of marginal edge portions overlapping each other disposed over the upper surface of the core. The marginal edge portions are hydrophillic to form a dual layer fluid acquisition system.

In accordance with one aspect of this invention the only portion of the layer of non-woven material which is hydrophillic is the marginal edge portions that are disposed over the upper surface of the core, e.g., the portion of the layer of non-woven material located between the hydrophillic marginal edge portions is hydrophobic.

In accordance with another aspect of this invention at least one additional layer of material forms a portion of the fluid acquisition system. The additional layer is located adjacent the overlapping marginal edge portions of the layer of non-woven material, e.g., is located on top of the overlapping portions, between the overlapping portions or below the overlapping portions. The additional layer may be a non-woven material and/or a three-dimensional apertured film.

In accordance with another aspect of this invention the core has a pair of marginal edges, with the hydrophillic portions of the non-woven layer being disposed inward of the marginal edge portions of the core.

In accordance with another aspect of this invention each of the overlapping portions of the layer of non-woven material extends the length of the core.

In accordance with another aspect of this invention the fluid acquisition system is made by providing a layer of a non-woven material having marginal edge portions, with each of the marginal edge portions being hydrophillic, and wrapping the core with the layer of non-woven material so that the marginal edge portions overlap each other over the upper surface of the core, whereupon the overlapping hydrophillic marginal edge portions form a dual layer fluid acquisition system.

DESCRIPTION OF THE DRAWING

FIG. 3 is an enlarged sectional view showing a portion of the absorbent article of FIG. 1, i.e., the core of the absorbent article and a fluid acquisition system constructed in accordance with this invention;

FIG. 4 is a sectional view, like that of FIG. 3, but showing the core of the absorbent article with an alternative embodiment of the fluid acquisition system constructed in accordance with this invention;

FIG. 7 is an enlarged sectional view showing a portion of the absorbent article of FIG. 5, i.e., the core of the absorbent article and a fluid acquisition system constructed in accordance with this invention;

FIG. 8 is a sectional view, like that of FIG. 7, but showing the core of the absorbent article with an alternative embodiment of the fluid acquisition system constructed in accordance with this invention;

DETAILED DESCRIPTION OF THE PREFERRED EMBODIMENT

Figure 1:
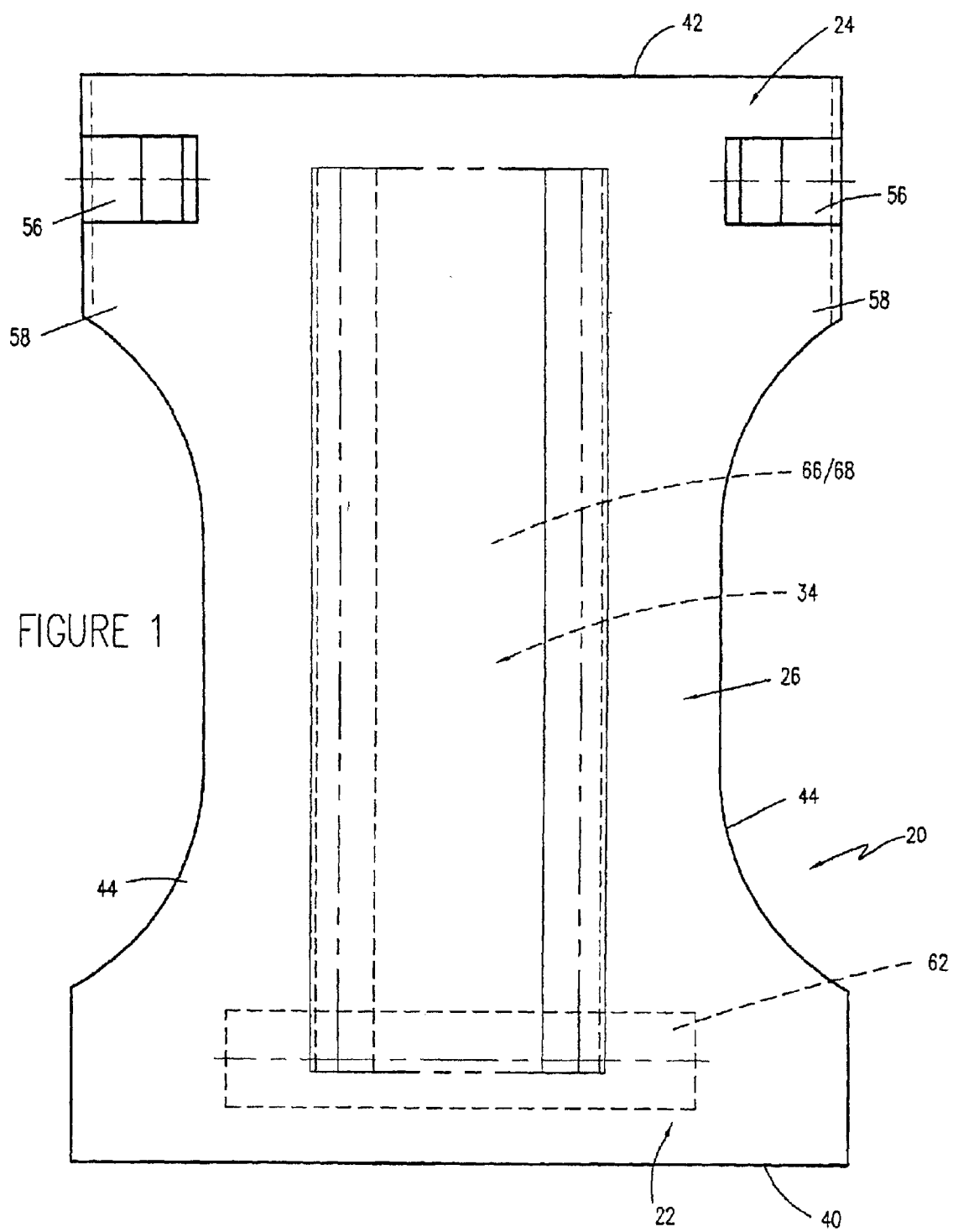
FIG. 1 is a plan view of one exemplary absorbent article, e.g., a diaper, constructed in accordance with this invention.

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a diaper. While the following description will focus on diapers, it should be clear that the subject invention can be used for any type of absorbent article or garment to be worn by a person for trapping urine or menses.

Figure 2:
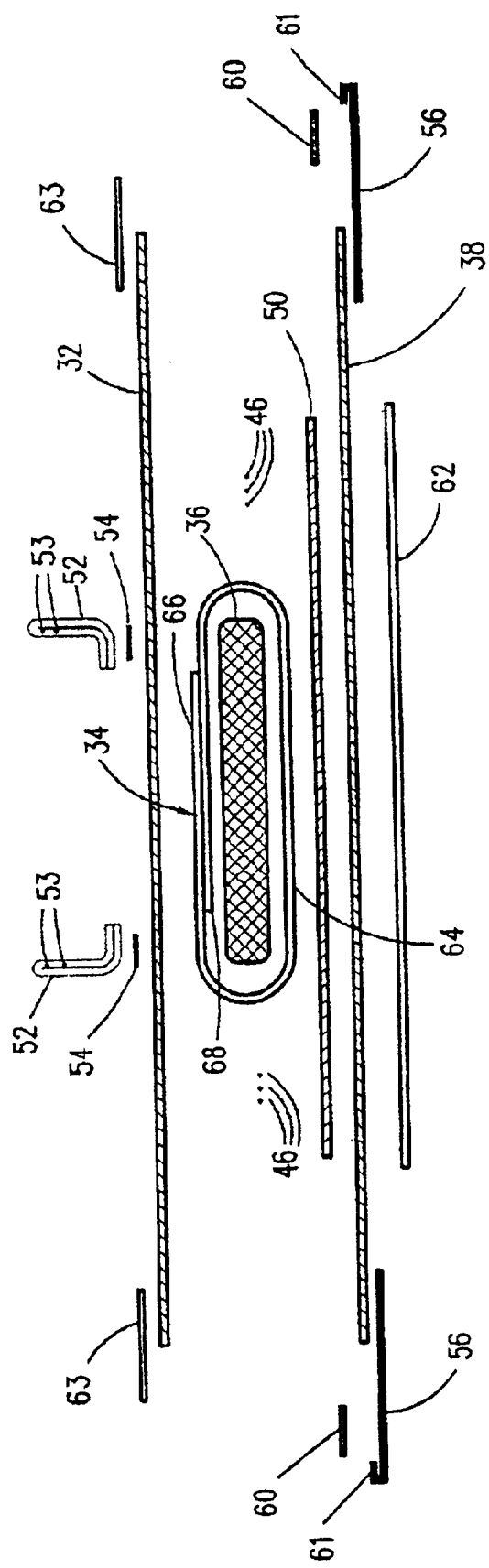
FIG. 2 is an exploded transverse sectional view of FIG. 1.
Figure 5:
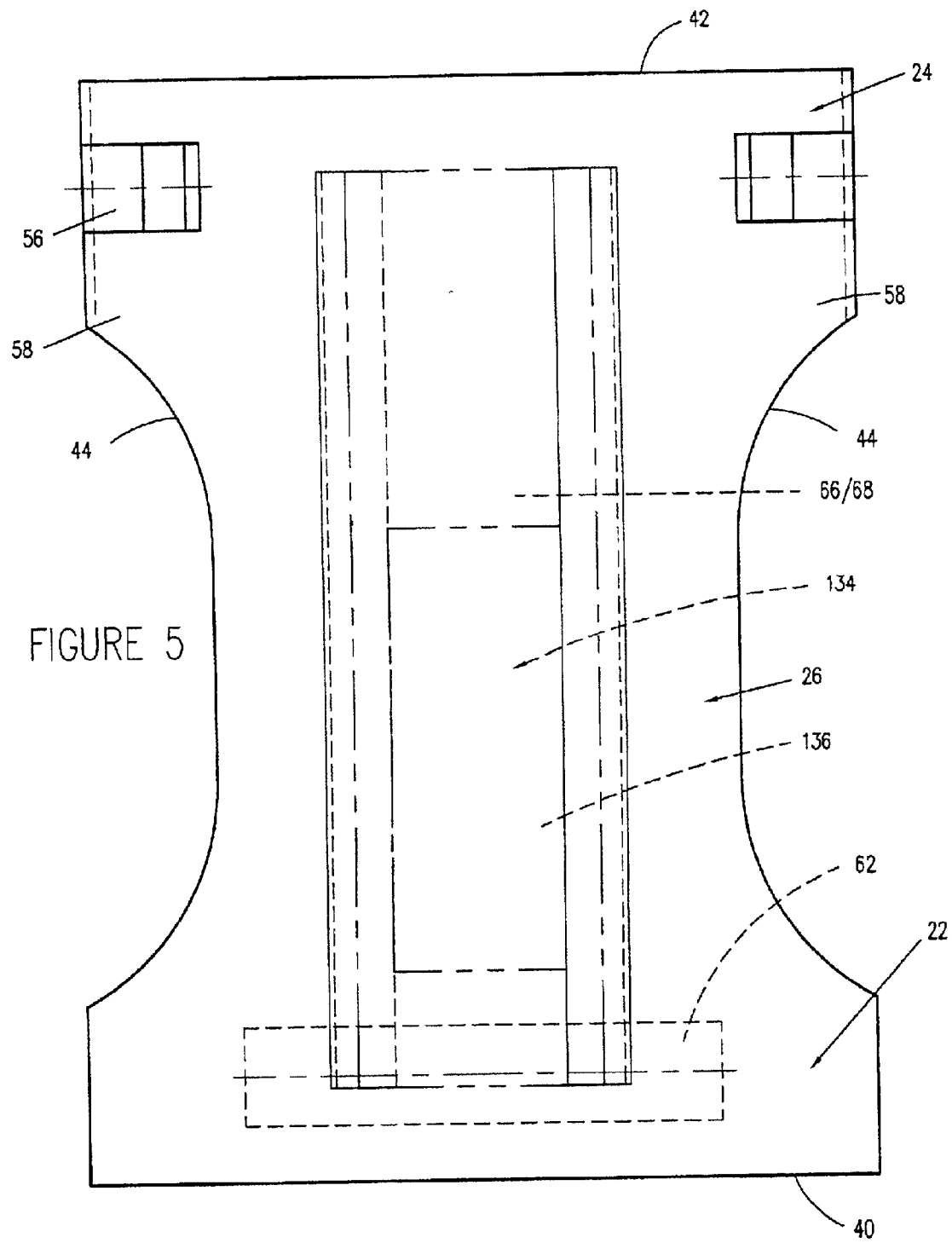
FIG. 5 is a plan view, like that of FIG. 1, but showing another exemplary absorbent article, e.g., a diaper, constructed in accordance with this invention.
Figure 6:
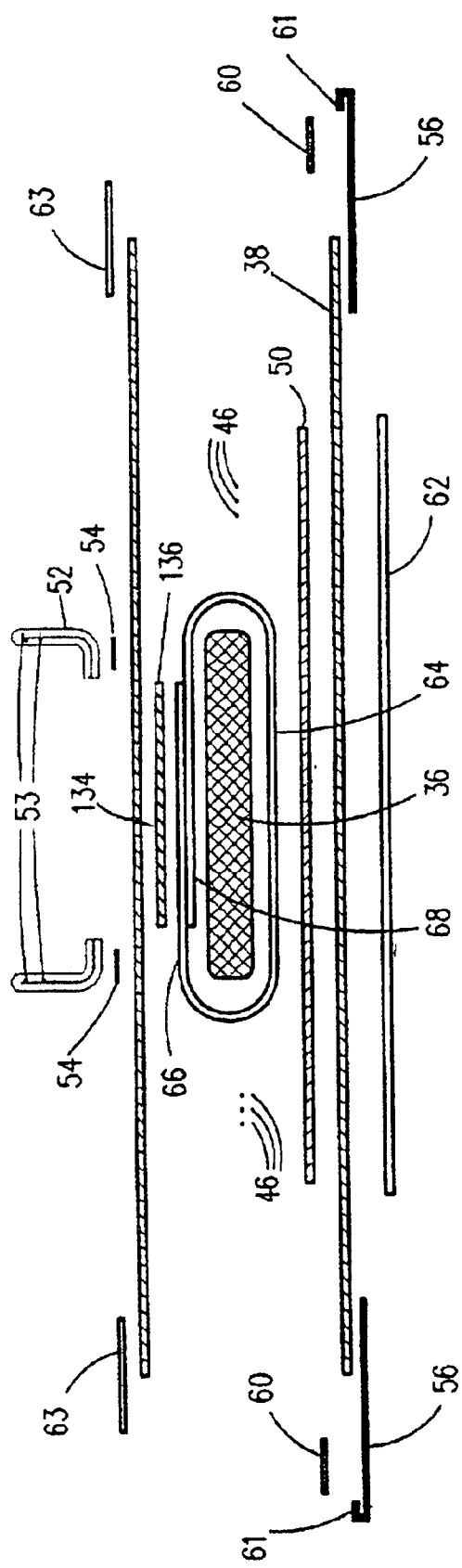
FIG. 6 is an exploded transverse sectional view, like that of FIG. 1, but of the embodiment of FIG. 5.

The diaper 20 basically comprises a chassis including a front waist portion 22, a back waist portion 24, and a crotch portion 26 and is of generally conventional construction, except for the inclusion of fluid acquisition system designated by the reference number for effectively transferring received body fluid(s) to an absorbent core capable of handling repeated insults of the fluid(s). In the exemplary embodiment to be described hereinafter the core can include a higher proportion of liquid-absorption-enhancing materials, e.g., SAP, in its absorbent core than commonly used in the prior art. Those components of the diaper 20 will be described in detail later. Prior to describing those components a brief description of the other portions of the diaper will now be discussed. To that end and as best seen in FIG. 2, the diaper 20 basically comprises a body-side liner or top sheet 32, the heretofore mentioned fluid acquisition system, designated by the reference number 34 and which will be described later, a liquid absorbent structure or core 36 including liquid-absorption-enhancing materials (also to be described later), and an outer cover or back sheet 38.

The top sheet 32 is arranged to face toward the body of the user when the diaper 20 is in place, with the back sheet 38 facing away from the wearer. The top sheet 32 is superimposed over the back sheet 38, with the absorbent core 36 interposed therebetween. The fluid-acquisition system 34 is in the form of a web of flexible material (to be described in detail later) which is wrapped about the core 36 so that the two marginal longitudinally extending side portions of the web of flexible material overlap each other on the top of the core and under the top sheet. These two overlapping portions are constructed such that they are hydrophyllic to cooperate to manage, transport, accommodate and/or direct high volumes and high flow rates of urine or other body fluid received from the top sheet "target" or fluid "insult" zone (i.e., the area at which the body fluid(s) gain(s) ingress into the diaper) into the absorbent core 36 at a rate that the core can handle, despite multiple insults of such fluid.

The top and back sheets, 32 and 38, respectively, are coextensive is size and shape and each comprises front edge 40, a back edge 42, and a pair of side edges 44. These two edges form the waist section of the diaper when it is worn. An elastic foam (not shown) can be located along the front edge and along the rear edge to elasticize the diaper's waist section. Each side edge 44 includes a central, cut-out to define a respective leg cut out. The crotch portion 26 of the diaper is located between the leg cut-outs. The top sheet 32 and/or back sheet 38 can be any suitable shape and dimensions for other designs or constructions, as will be clear to those skilled in the art.

The top sheet 32 is bonded to the back sheet 38 around its entire periphery, with the absorbent material core 36 and the fluid acquisition system 34 interposed therebetween. The back sheet and top sheet can be joined together in any suitable manner, e.g, by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

Each lateral side edge 44 of the diaper 20 is elasticized by means of plural, e.g., three, longitudinally extending elastic, e.g., LYCRA 940 decitex, threads or strands 46 (FIG. 2) disposed along the length of the cut away portion of that side edge. The strands may be obtained from E.I. DuPont de Nemours and Company, Wilmington, Del., and are held in place by a suitable elastic adhesive, such as that used to hold the elastic foam of the waist portion in place. The elastic adhesive is intermittently applied along the top sheet to allow the diaper to be actively stretchable along the leg cut outs and not all the way to the edges of the respective waist portions, thereby enable the diaper to closely conform about the legs of the wearer for impeding the egress of waste material from the crotch region, as is conventional. Other arrangements can be used to elasticize the sides of the crotch portion of the diaper. For example, in lieu of plural longitudinally extending elastic threads 46, multiple strands of elastic material can be arranged in other orientations, intersecting, diagonal, or any combination thereof, or can be a film or laminate of various types of elastomeric material.

The back sheet 38 or cover is preferably formed of a laminated sheet of a non-woven material and a film 50 (with the non-woven side positioned as the outermost layer). The film layer 50 is centered in the diaper and extends the length of the diaper, i.e., from the front edge 40 to the back edge 44 and for a substantial width of the diaper as best seen in FIG.

2. The material of the back sheet should be hydrophobic, soft in texture, and strong in tensile strength. One particularly suitable material is a spunbond-meltblow-spunbond (SMS) web, available from AVGOL Nonwoven Industries LTD., Holon, Israel. The spunbond layer is made of polypropylene fibers. Such composites provide the dual advantages of liquid barrier properties of film along with a soft, warm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylene/polyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the back sheet 38 may include polypropylene films, co-extruded films (polyethylene and ethylene vinyl acetate), co-polymer films (polyethylene/polypropylene), and polylaminates (polypropylene non-woven and polyethylene film). Still another example is a film made of a "breathable' microporous polyethylene. Suitable breathable films are available from Exxon Chemical Company, Buffalo Grove, Ill. This material allows water vapor to pass through it over time, while being impervious to liquids. The water vapor transmission rate may range from 200–2000 grams per square meter per 24-hour period.

In order to enable urine to quickly and efficiently pass through the top sheet 32 and into the underlying acquisition system 34 for subsequent transference to the absorbent core 36 for trapping therein, the top sheet 32 is preferably liquid permeable (hydrophyllic). In particular, the top sheet may be selected from a variety of textile-like films and fabrics. Suitable fabrics include non-woven materials that are pervious to liquid, soft and pliable. Preferred non-woven materials include spun-bonded polypropylene; spunbonded polyethylene; thermally bonded webs of staple fibers preferably polypropylene shape or sheath/core bi-component fibers having a core of polyester or polypropylene and a sheath of polyethylene. To enhance the fluid control properties of the aforementioned liners, surfactants or wetting agents typified by X-100 and Triton X-102 available from Rohm & Haas Company of Philadelphia, Pa. may be applied to the fluid receiving zones of the liner selectively having the outer zones untreated to reduce migration excreted fluid such as urine into the outer diaper regions leading to diaper leakage. If desired, the top sheet 32 may be formed of a liquid impermeable material having plural apertures or pores extending therethrough so as to make the material liquid permeable.

The absorbent core 36 is a rectangular member which is centered in the diaper and extends from close to the front waist edge 40 to close to the back waist edge 42. The core 36 can be made up of any suitable absorbent material, as well as combinations of different types of absorbent material(s). For example, in the preferred embodiments shown herein the absorbent core 36 is formed of a mixture of pulp fluff and SAP. Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP 2260. The super absorbent materials can be in various geometric forms, such as various shaped particles, fibers, foams, and layers. The fluff and SAP are present in a ratio of about 11.5 grams of SAP to 16.5 gms of fluff for a size 4 diaper, and have a core density range of about 0.16 to 0.18 grams per cubic centimeter.

Moreover, the core 36 can be of any shape and can be a single, integral absorbent structure, or can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. If desired the absorbent core can sandwiched between one or two plies of tissue (not 5 shown). Although such an arrangement is not necessary since one component making up the fluid acquisition system 34 is wrapped about the core as will be described later. The absorbent core is centered along the transverse direction and registered in the machine (longitudinal) direction within the diaper's chassis.

The amount of each absorbent material and SAP/fluff ratio depends on the size of the brief, e.g., "Small", "Medium", "Large" or "Extra Large" and the construction of the liquid acquisition or transfer system 34.

As seen in FIG. 2 the diaper 20 also includes a pair of conventional "standing leg gathers" or cuffs 52 or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized by plural elastic threads 53 and extends from the edge of the front waist portion to the edge of the rear waist portion and along a respective side marginal edges of the core 36 and upstanding from the top sheet 32. The standing leg gathers are secured in place by a suitable adhesive, e.g., construction adhesive 54.

The diaper 20 is arranged to be held in place on the body of the wearer in a conventional manner, e.g., by means of a pair of fastening tabs or tapes 56 projecting outward from a pair of respective ear portions 58 forming the side edges of top sheet 32 of the diaper contiguous with its back waist section (i.e., edge 42). In particular, each tab 56 includes a patch 60 of a myriad of small hooks on its underside surface. Each tab includes a free end 61 in the form of a finger lift area. A pair of release tapes 63 are also provided attached to the respective marginal sides of the top sheet to temporarily hold respective tabs 56 thereon until the tabs are read for use. To that end, each patch 60 is arranged to be releasably secured to a "landing zone" portion 62 (FIGS. 1 and 2) on the outer cover 38 in the front waist region of the diaper. The landing zone 62 is located at a position so that when the diaper is folded in half with the front waist portion disposed opposite the back waist portion, the landing zone 62 will be aligned with the tabs 56. The landing zone 62 basically comprises a rectangular panel of whose outer surface comprises a myriad of small loops arranged to be engaged by the small hooks of the patch 60 of each fastening tab.

When the diaper is in place on the wearer with the front waist portion disposed over the lower abdomen, the back waist portion disposed over the lower back and buttocks region, and the crotch portion between the legs, each tab 56 may be brought into engagement with the a portion of the landing zone 62 closest to that tab on the front portion of the diaper so that the myriad of hooks on the patch 60 engage the myriad of loops of the landing zone 62 to releasably secure the tab thereto. Any suitable multi-hook and multi-loop materials may be used. Particularly suitable multi-hook patches 60 are available from YKK (U.S.A.), Inc., Marietta, Ga., under the model designation Microhook (D-7) or Mac-rohook (EL "B"), while particularly a suitable multiloop material is a polyester fiber material having a basis weight of 1.55 ounce per square yard with a laminated polypropylene film (8 mil.) backing is available from FAB Industries, Inc, New York, N.Y.

Alternatively the tabs 56 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

As mentioned earlier, the fluid-acquisition system 34 basically comprises at least two layers disposed over each other. In the exemplary embodiment of diaper 20 shown in FIGS. 1–4 the at least two layers are, in fact, only two layers. Those two layers are formed by overlapping portions of a web 64 of a non-woven material, that is wrapped about the core 36 so that the longitudinally extending marginal edge portions 66 and 68 of the web 64 overlap each other on the top surface of the core 36. In other embodiments, e.g., the embodiments of FIGS. 5–11, of this invention there is at least one more layer in the fluid acquisition system in addition to the layers formed by the end portions 66 and 68. Those alternative embodiments will be described later.

If desired the core 36 with the non-woven material web wrapped about it may be held in place by a hydrophillic construction adhesive, such as Cycloflex from National Starch and Chemical Corporation, Bridgewater, N.J. In such an arrangement the adhesive may be applied on undersurface of the layer 64 or on the underlying layer, e.g., layer 50 (if that layer is used) or directly on the inner surface of the back sheet 38 (if layer 50 isn't used).

The non-woven material web 64 making up two of the layers of the fluid acquisition system 34 can be any type of fibrous material like those used in prior art diapers or other absorbent articles. Preferred non-woven materials include spun-bonded polypropylene; spunbonded polyethylene; thermally bonded webs of staple fibers preferably polypropylene shape or sheath/core bi-component fibers having a core of polyester or polypropylene and a sheath of polyethylene., e.g., a through-air bonded/carded web, a spun-bond bi-component non-woven web, a web of cross-linked cellulosic fibers. As will be recognized by those skilled in the art, the foregoing materials for the web are hydrophobic. Thus, in accordance with the embodiment shown in FIG. 1 the overlapping portions 66 and 68 of the web 64 are treated with a surfactant or wetting agent to render them hydrophyllic. One particularly suitable surfactant is available from Rohm & Haas Company of Philadelphia, Pa. under the trade designation Triton X-100. The surfactant may be applied to the web material by surface treatment, e.g., sprayed on, or the web can be immersed in the surfactant. In fact, the surfactant may be incorporated into the fibers of the material, if desired.

In the embodiment of the fluid acquisition system of FIG. 1 the upper layer 66 is coextensive in size with the lower layer 68, as shown clearly in the enlarged cross sectional view of FIG. 3. The width of the upper and lower layers 66 and 68, respectively, is slightly less than the width of the core 36, provided that it is at least as wide as the insult or target zone and is confined thereto. As will be appreciated by those skilled in the art the target zone of an absorbent article, such as a diaper, a panti-liner, etc., is typically of a smaller area than the absorbent core 36 of that article and is located in a generally centered position with respect to the sides of the core and may be centered or off-centered with respect to the ends of the core. If desired, the overlapping layers 66 and 68 can be the same width as the core 36. The entire length of the upper and lower layers 66 and 68 can be hydrophyllic or only the portions of those layers which are within the insult or target zone can be hydrophyllic. In the embodiment shown the marginal edge portions forming the overlapping layers 66 and 68 are preferably hydrophyllic along the entire length of the core 36.

As should be appreciated by those skilled in the art, since only the overlapping portions 66 and 68 of the web 64 are hydrophyllic, while the remaining portions, designated by the reference number 64A are hydrophobic, those remaining hydrophobic portions 64A of the web 64 that wrap about the core 36 will prevent the egress of liquid from the core through the web out of the sides and bottom of the core.

Figure 11:
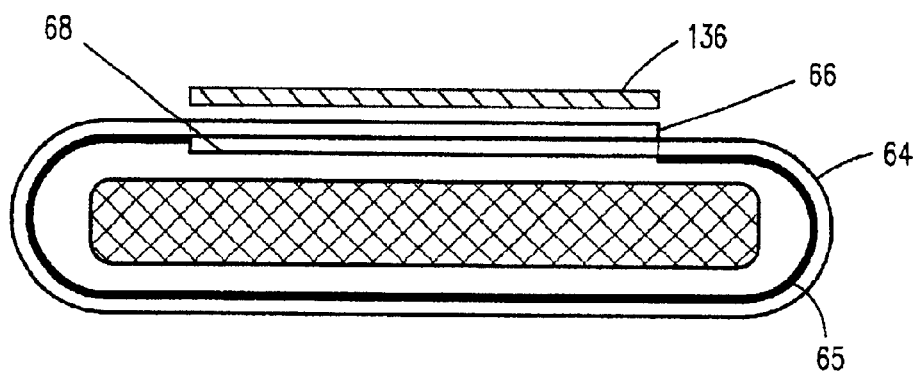
FIG. 11 is a sectional view, like that of FIGS. 7–10, but showing the core of the absorbent article with yet another alternative embodiment of the fluid acquisition system constructed in accordance with this invention.

As an alternative to the embodiment of FIGS. 1–3 the entire web 64 may be treated to make it hydrophyllic over its entire area. Such an arrangement is shown in the embodiment of FIG. 4 where the fully hydrophyllic web is denoted by the reference number 64B. When using a fluid acquisition system comparing a layer like that of 64B, means should be provided to prevent liquid from the core 36 from exiting through the diaper's back sheet 38. Use of a hydrophobic layer, like the layer 50 on the inner surface of the back sheet 38 will serve this purpose. Other hydrophobic barriers can be used in lieu of the layer 50, if desired. For example the inner surface of the web 64 may have a hydrophobic layer, e.g., a film 65, secured thereto as shown in FIG. 11. In particular, the film layer 65 is secured on the inner surface of the web 64 in all areas except for the area where the portions 66 and 68 overlap, i.e., the fluid acquisition layers.

If desired, the fluid acquisition system of this invention may include one or more additional layers to facilitate transfer and spread of the liquid insult into the core 36. For example, in FIGS. 5–11 there are shown alternative embodiments of a diaper 200 using a three layer fluid acquisition system 134 constructed in accordance with this invention. The diaper 200 is virtually the same as the diaper 20, except for the use of the three layer fluid acquisition system 134. To that end in the interests of brevity the common structural elements of the diapers 20 and 200 will be given the same reference numbers and the details of the construction and operation of those elements will not be reiterated.

As can best be seen the diaper 200 basically comprises a body-side liner or top sheet 32, the heretofore mentioned fluid acquisition system 134, a liquid absorbent core 36, and an outer cover or back sheet 38. The top and back sheets are coextensive is size and shape and each comprises front edge 40, a back edge 42, and a pair of side edges 44. Each side edge includes a central leg cut out. The top sheet 32 is liquid permeable and is bonded to the back sheet 38, with the absorbent material core 36 and the fluid acquisition system 134 interposed between the back sheet and the top sheet. The fluid acquisition system 134 is located below the top sheet 32 and over the core 36. The back sheet 38 is formed of a laminated sheet of a non-woven material and a film 50, with the non-woven side positioned as the outermost layer. The absorbent core 36 is a rectangular member which is centered in the diaper 200 and extends from close to the front waist edge 40 to close to the back waist edge 42. The diaper 20 is arranged to be held in place on the body of the wearer by a pair of fastening tapes 56 projecting outward from the ear portions 58 for releasable engagement with the landing zone 62 located on the back sheet at the front waist portion.

The exemplary fluid-acquisition system 134 of the embodiments of FIGS. 5–11 comprises a modification of the fluid acquisition system 34 described above, e.g., system 134 includes at three layers disposed on top of one another over the core 36. In particular, two of the layers of the system 134 are made up by overlapping portions 66 and 68 of a web 64 of non-woven material that is wrapped about the core 36 so that the longitudinally extending marginal edge portions 66 and 68 of the web 64 overlap each other on the top surface of the core 36. A third layer is provided by a "cut and place" patch 136 of any other suitable material for use in a fluid acquisition system. The patch or third acquisition layer 136 may merely be disposed at its desired location or may secured in place by means of a suitable adhesive, e.g., a construction adhesive.

Since the fluid acquisition system 134 is a modification of the system 34, the common details of the components of those two systems will be given the same reference numbers and the details of their construction and operation will not be reiterated in the interest of brevity. Thus, as can best be seen in FIGS. 5–11, the third layer 136 of the fluid acquisition system 134 is in the form of a rectangular patch of an apertured polymeric layer (film). In particular, the apertured polymeric film patch 136 includes a myriad of very tiny conically shaped apertures, which taper in the direction from the top sheet 32 towards the core 36. These three-dimensionally shaped apertures serve direct the fluid insult inwardly towards the core 36. The patch of apertured film 136 is preferably located at the insult zone as best seen in the plan view of FIG. 5. If desired, the acquisition system 134 can be extended into the rear portion of the diaper, as well so that it is not confined to the insult zone.

In the embodiment of FIGS. 5–8 and 11, the fluid acquisition layer 136 is disposed immediately below the top sheet 32 and above the fluid acquisition layer 66 formed by the overlapping portion of the web 64. The web 64 is constructed to include a hydrophobic portion 64A located between the overlapping hydrophilic marginal side portions 66 and 68, as described above. In the embodiment of FIG. 8, the additional acquisition layer 136 is disposed immediately below the top sheet 32 and above the layer 66 like the embodiment of FIG. 7. So too, in the embodiment of FIG. 11, the additional acquisition layer 136 is disposed immediately below the top sheet 32 and above the layer 66. As should be appreciated by those skilled in the art the use of the additional fluid acquisition layer 136 in the embodiments of FIGS. 5–8 and 11 results in a relatively fast and high fluid volume intake into the core and a slower and lower fluid volume output after the core has been saturated with fluid and exposed to compressive forces, i.e., the apertured film layer 136 will tend to prevent liquid from flowing out of the core 36 back through the top sheet 32.

Figure 9:
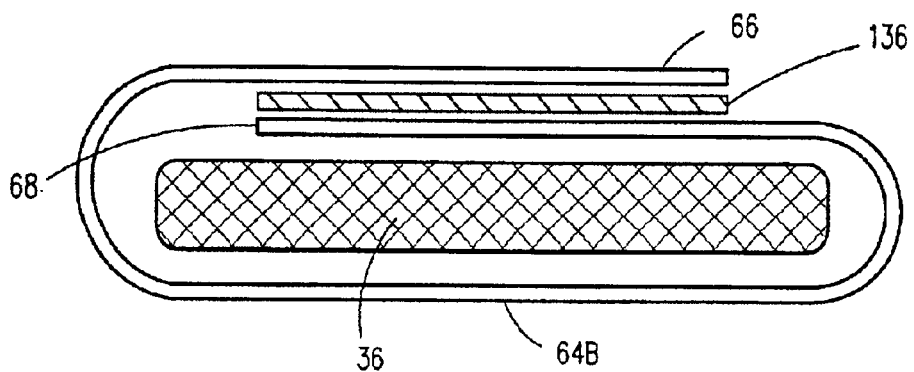
FIG. 9 is a sectional view, like that of FIGS. 7 and 8, but showing the core of the absorbent article with another alternative embodiment of the fluid acquisition system constructed in accordance with this invention.
Figure 10:
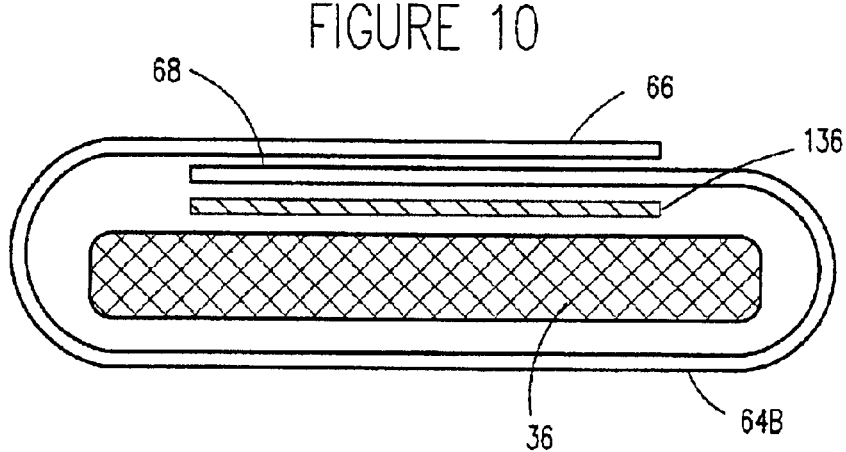
FIG. 10 is a sectional view, like that of FIGS. 7–9, but showing the core of the absorbent article with still another alternative embodiment of the fluid acquisition system constructed in accordance with this invention.

Notwithstanding the above the third acquisition layer 136 need not be located on top of the acquisition layer 66. To that end as shown in FIG. 9, the additional acquisition layer 136 is disposed between the acquisition layers 66 and 68. In the embodiment of FIG. 10 the additional or third layer 136 is disposed under the acquisition layer 66 and directly over the core 36. Like the embodiments of FIGS. 5–8 the use of the apertured film acquisition layer 136 in these alternative locations still tends to prevent "re-wet" (i.e., liquid from flowing out of the core back through the top sheet).

It should also be pointed out at this juncture that alternative embodiments of the fluid acquisition system of this invention can include more than three layers, if desired. Moreover the web 64 and its overlapping portions 66 and 68 can be constructed in accordance with any of the embodiments disclosed heretofore, e.g., FIGS. 3, 4 and 11. Further still, the various arrangements of the multi-layer fluid acquisition system need not be constructed as shown or described above. Thus, for example the web of material wrapping the core can be reverse zone coated to create a natural repellant barrier on the sides and back (underside) of the core. While the use of hydrophobic area(s) for the wrapping web is (are) in many cases desirable, it (they) are not mandatory, so long as the absorbent article in which the core and fluid acquisition layer are to be used includes some means for preventing liquid from exiting the core at its sides or bottom.

As should be appreciated from the foregoing the fluid acquisition system of this invention optimizes the fluid penetration rate and volume into the absorbent core 36 below it, while also minimizing the fluid from exiting the diaper 20 when it is saturated and under high stress. The result is a diaper or other absorbent article which exhibits high fluid intake and low fluid rewet characteristics, features which are desirable to obtain high absorbency performance with minimal fluid exposure to the wearer's skin. Moreover, the fluid acquisition system can be readily made by merely wrapping the core of the article with a suitably constructed web of material so that marginal edge portions overlap the core, and with at least some portions of the overlapping portions being constructed to be hydrophilic to facilitate entry of the liquid insult into the core. This arrangement should eliminate the need for using a conventional tissue wrap about the core, as has characterized the prior art. As is known, use of a tissue wrap brings with it the tendency to have leakage from the absorbent article since the tissue itself tends to give up fluid retained in it quite easily. Moreover, the material making up the core wrap of this invention is considerably stronger than conventional tissue wrap. Accordingly, highly efficient and effective absorbent articles can be fabricated and assembled more easily and inexpensively than heretofore accomplished using conventional tissue wraps. Further still, the fabrication of absorbent articles using cut and place multi-layer acquisition systems comprising high basis weight non-wovens and/or two or three dimensional apertured films, as has characterized the prior art, is relatively complex and concomitantly expensive to achieve. The subject invention overcomes that disadvantage since the same or similar basis weight fluid acquisition system may be obtained by wrapping the appropriately configured acquisition layer material about the core.

Without further elaboration the foregoing will so fully illustrate our invention that others may, by applying current or future knowledge, adopt the same for use under various conditions of service.

We claim:

1. A disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, said marginal edge portions overlapping substantially the entire width of said core and being hydrophillic to form a dual layer fluid acquisition system.

2. The disposable absorbent article of claim 1 wherein said dual acquisition system is defined by the entire area where said marginal edge portions overlap each other.

3. The disposable absorbent article of claim 1 comprising an additional layer of material forming a portion of said fluid acquisition system, said additional layer being located adjacent said overlapping marginal edge portions of said layer of non-woven material.

4. The disposable absorbent article of claim 3 wherein said additional layer is selected from the group consisting of a non-woven material and a three-dimensional apertured film.

5. The disposable absorbent article of claim 4 wherein said additional layer is located on top of said overlapping marginal edge portions.

6. The disposable absorbent article of claim 1 wherein said layer of non-woven material is treated across its entire surface area to render it hydrophillic.

7. The disposable absorbent article of claim 1 wherein said layer of non-woven material is treated across only its marginal edge portions to render such portions hydrophillic.

8. The disposable absorbent article of claim 6 additionally comprising a layer of a hydrophobic material located between said core and said back sheet.

9. A disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, said marginal edge portions being hydrophillic to form a dual layer fluid acquisition system and wherein the only portion of said layer of non-woven material which is hydrophillic is said marginal edge portions that are disposed over said upper surface of said core.

10. The disposable absorbent article of claim 9 wherein the portion of said layer of non-woven material is located under said core.

11. The disposable absorbent article of claim 10 wherein said hydrophobic portion of said non-woven material located between said hydrophilic marginal edge portions is hydrophobic.

12. A disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, and an additional layer of material located between said overlapping marginal edge portions and selected from the group consisting of a non-woven material and a three-dimensional apertured film, said marginal edge portions being hydrophillic to form a dual layer fluid acquisition system.

13. A disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, and an additional layer of material located below said overlapping marginal edge portions and above said upper surface of said core, said additional layer being selected from the group consisting of a non-woven material and a three-dimensional apertured film, said marginal edge portions being hydrophillic to form a dual layer fluid acquisition system.

14. A disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a pair of marginal edges, a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, said marginal edge portions being hydrophillic to form a dual layer fluid acquisition system, said hydrophillic portions of said non-woven layer are disposed inward of said marginal edge portions of said core.

15. The disposable absorbent article of claim 14 wherein the portion of said layer of non-woven material located between said hydrophillic marginal edge portions is hydrophobic.

16. A disposable absorbent arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said too sheet and a bottom surface adjacent said back sheet, said fluid acquisition system comprising a layer of a non-woven material wrapped about said core and having a pair of marginal edge portions overlapping each other disposed over said upper surface of said core, said marginal edge portion being hydrophillic to form a dual layer fluid acquisition system wherein the only portion of said layer of non-woven material which is hydrophillic is said marginal edge portions that are disposed over said upper surface of said core and wherein the portion of said layer of non-woven material located between said hydrophillic marginal edge portions is hydrophobic, with a portion of said hydrophobic portion of said non-woven material being located over said core and extending beyond said overlapping portions up to the marginal edges of said core and under said core.

17. A The disposable absorbent article arranged to be worn by a wearer to trap and collect fluid waste products of the wearer, said article comprising a top sheet, a fluid acquisition system, a fluid absorbent core, and a back sheet, said top sheet being disposed over said core, said core having a top surface located adjacent said top sheet and a bottom surface adjacent said back sheet, said fluid acquisition system comprising a layer of a non-woven material wrapped about said core and having a pair of marginal edge portions overlapping each other disposed over said upper surface of said core, said marginal edge portions being hydrophillic to form a dual layer fluid acquisition system and wherein each of said overlapping portions of said non-woven material extends the length of said core.

18. The disposable absorbent article of claim 17 comprising an additional layer of material forming a portion of said fluid acquisition system, said additional layer being located adjacent said overlapping marginal edge portions of said layer of non-woven material and being of a lesser length than said core.

19. The disposable absorbent article of claim 18 wherein said additional layer is selected from the group consisting of a non-woven material and a three-dimensional apertured film.

20. The disposable absorbent article of claim 19 wherein said additional layer is located between said overlapping marginal edge portions.

21. The disposable absorbent article of claim 19 wherein said additional layer is located on top of said overlapping marginal edge portions.

22. The disposable absorbent article of claim 19 wherein said additional layer is located below said overlapping marginal edge portions and above said upper surface of said core.

23. A fluid acquisition system for use in a disposable absorbent article arranged to be worn by a wearer to trap and collect fluid waste products of the wearer, the article comprising a top sheet, a fluid absorbent core, a back sheet, the top sheet being disposed over the core, the core having a top surface located adjacent the top sheet and a bottom surface adjacent the back sheet, said fluid acquisition system comprising a layer of a non-woven material wrapped about said core and having a pair of marginal edge portions overlapping each other disposed over the upper surface of the core, said marginal edge portions overlapping substantially the entire width of said core and being hydrophillic to form a dual layer fluid acquisition system.

24. The fluid acquisition system of claim 23 wherein said dual acquisition system is defined by the entire area where said marginal edge portions overlap each other.

25. The fluid acquisition system of claim 23 wherein said layer of non-woven material is treated across its entire surface area to render it hydrophillic.

26. A fluid acquisition system for use in a disposable absorbent article arranged to be worn by a wearer to trap and collect fluid waste products of the wearer, the article comprising a top sheet, a fluid acquisition system, a fluid absorbent core, and a back sheet, the top sheet being disposed over the core, the core having a top surface located adjacent the top sheet and a bottom surface adjacent the back sheet, said fluid acquisition system comprising a layer of a non-woven material wrapped about the core and having a pair of marginal edge portions overlapping each other disposed over the upper surface of the core, said marginal edge portions being hydrophillic to form a dual layer fluid acquisition system and wherein the only portion of said layer of non-woven material which is hydrophillic is said marginal edge portions that are disposed over the upper surface of the core.

27. The fluid acquisition system of claim 26 wherein the portion of said layer of non-woven material located between said hydrophillic marginal edge portions is hydrophobic.

28. The fluid acquisition system of claim 27 wherein said hydrophobic portion of said non-woven material is located under said core.

29. A fluid acquisition system for use in a disposable absorbent article arranged to be worn by a wearer to trap and collect fluid waste products of the wearer, the article comprising a top sheet, a fluid acquisition system, a fluid absorbent core, and a back sheet, the top sheet being disposed over the core, the core having a top surface located adjacent the top sheet and a bottom surface adjacent the back sheet, said fluid acquisition system comprising a layer of a non-woven material wrapped about the core and having a pair of marginal edge portions overlapping each other disposed over the upper surface of the core, said marginal edge portions being hydrophillic to form a dual layer fluid acquisition system, said fluid dual layer fluid acquisition system comprising an additional layer of material located adjacent said overlapping marginal edge portions of said layer of non-woven material.

30. The fluid acquisition system of claim 29 wherein said additional layer is selected from the group consisting of a non-woven material and a three-dimensional apertured film.

31. The fluid acquisition system of claim 30 wherein said additional layer is located between said overlapping marginal edge portions.

32. The fluid acquisition system of claim 30 wherein said additional layer is located on top of said overlapping marginal edge portions.

33. The fluid acquisition system of claim 30 wherein said additional layer is located below said overlapping marginal edge portions.

34. A The fluid acquisition system for use in a disposable absorbent article arranged to be worn by a wearer to trap and collect fluid waste products of the wearer, the article comprising a top sheet, a fluid acquisition system, a fluid absorbent core, and a back sheet, the top sheet being disposed over the core, the core has a pair of marginal edges, a top surface located adjacent the top sheet and a bottom surface adjacent the back sheet, said fluid acquisition system comprising a layer of a non-woven material wrapped about the core and having a pair of marginal edge portions overlapping each other disposed over the upper surface of the core, said marginal edge portions being hydrophillic to form a dual layer fluid acquisition system, said hydrophillic portions of said non-woven layer being arranged to be disposed inward of the marginal edge portions of the core.

35. The fluid acquisition system of claim 34 wherein the portion of said layer of non-woven material located between said hydrophillic marginal edge portions is hydrophobic.

36. A The fluid acquisition system for use in a disposable absorbent article arranged to be worn by a wearer to trap and collect fluid waste products of the wearer, the article comprising a top sheet, a fluid acquisition system, a fluid absorbent core, and a back sheet, the top sheet being disposed over the core, the core having a top surface located adjacent the top sheet and a bottom surface adjacent the back sheet, said fluid acquisition system comprising a layer of a non-woven material wrapped about the core and having a pair of marginal edge portions overlapping each other disposed over the upper surface of the core, said marginal edge portions being hydrophillic to form a dual layer fluid acquisition system, each of said overlapping portions of said non-woven material being arranged to extend the length of the core.

37. The fluid acquisition system of claim 36 comprising an additional layer of material forming a portion of said fluid acquisition system, said additional layer being located adjacent said overlapping marginal edge portions of said layer of non-woven material and arranged to be of a lesser length than the core.

38. The fluid acquisition system of claim 37 wherein said additional layer is selected from the group consisting of a non-woven material and a three-dimensional apertured film.

39. The fluid acquisition system of claim 38 wherein said additional layer is located between said overlapping marginal edge portions.

40. The fluid acquisition system of claim 38 wherein said additional layer is located on top of said overlapping marginal edge portions.

41. The fluid acquisition system of claim 38 wherein said additional layer is located below said overlapping marginal edge portions.

42. A fluid acquisition system for use in a disposable absorbent article arranged to be worn by a wearer to trap and collect fluid waste products of the wearer, the article comprising a top sheet, a fluid acquisition system, a fluid absorbent core, and a back sheet, the top sheet being disposed over the core, the core having a top surface located adjacent the top sheet and a bottom surface adjacent the back sheet, said fluid acquisition system comprising a layer of a non-woven material wrapped about the core and having a pair of marginal edge portions overlapping each other disposed over the upper surface of the core, said marginal edge portions being hydrophillic to form a dual layer fluid acquisition system, said layer of non-woven material being treated across only its marginal edge portions to render such portions hydrophillic.

43. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a top surface arranged to be located adjacent said top sheet and a bottom surface arranged to be adjacent said back sheet, said method comprising:
(A) providing a layer of a non-woven material having marginal edge portions, each of said marginal edge portions being hydrophillic; and
(B) wrapping said core with said layer of said non-woven material so that said marginal edge portions overlap each other over said upper surface of said core, with said marginal edge portions overlapping substantially the entire width of said core, whereupon said overlapping hydrophillic marginal edge portions form a dual layer fluid acquisition system.

44. The method of claim 43 additionally comprising:
(C) providing an additional layer of material forming a portion of said fluid acquisition system, said additional layer being located adjacent said overlapping marginal edge portions of said layer of non-woven material.

45. The method of claim 44 wherein said additional layer is selected from the group consisting of a non-woven material and three-dimensional apertured film.

46. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a top surface arranged to be located adjacent said top sheet and a bottom surface arranged to be adjacent said back sheet, said method comprising:
(A) providing a layer of a non-woven material having marginal edge portions, each of said marginal edge portions being hydrophillic; and
(B) wrapping said core with said layer of said non-woven material so that said marginal edge portions overlay each other over said upper surface of said core, whereupon said overlapping hydrophillic marginal edge portions form a dual layer fluid acquisition system with the only portion of said layer of non-woven material which is hydrophillic being said marginal edge portions that are disposed over said upper surface of said core.

47. The method of claim 46 wherein the portion of said layer of non-woven material located between said hydrophillic marginal edge portions is hydrophobic.

48. The method of claim 47 wherein said hydrophobic portion of said non-woven material is located under said core.

49. The method of claim 45 wherein said additional layer is located on top of said overlapping marginal edge portions.

50. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a top surface arranged to be located adjacent said top sheet and a bottom surface arranged to be adjacent said back sheet, said method comprising:
(A) providing a layer of a non-woven material having marginal edge portions, each of said marginal edge portions being hydrophillic; and
(B) wrapping said core with said layer of said non-woven material so that said marginal edge portions overlap each other over said upper surface of said core, whereupon said overlapping hydrophillic marginal edge portions form a dual layer fluid acquisition system; and
(C) providing an additional layer of material forming a portion of said fluid acquisition system, said additional layer located between said overlapping marginal edge portions and is selected from the group consisting of a non-woven material and a three-dimensional apertured film.

51. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a top surface arranged to be located adjacent said top sheet and a bottom surface arranged to be adjacent said back sheet, said method comprising:
(A) providing a layer of a non-woven material having marginal edge portions, each of said marginal edge portions being hydrophillic; and
(B) wrapping said core with said layer of said non-woven material so that said marginal edge portions overlap each other over said upper surface of said core, whereupon said overlapping hydrophillic marginal edge portions form a dual layer fluid acquisition system; and
(C) providing an additional layer of material forming a portion of said fluid acquisition system, said additional layer located below said overlapping marginal edge portions and is selected from the group consisting of a non-woven material and a three-dimensional apertured film.

52. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a pair of marginal edges, a top surface arranged to be located adjacent said top sheet and a bottom surface arranged to be adjacent said back sheet, said method comprising:
(A) providing a layer of a non-woven material having marginal edge portions, each of said marginal edge portions being hydrophillic; and (B) wrapping said core with said layer of said non-woven material so that said marginal edge portions overlap each other over said upper surface of said core, whereupon said overlapping hydrophillic marginal edge portions form a dual layer fluid acquisition system and wherein said hydrophillic portions of said non-woven layer are disposed inward of said marginal edge portions of said core.

53. The method of claim 52 wherein the portion of said layer of non-woven material located between said hydrophillic marginal edge portions is hydrophobic.

54. A method of making a fluid acquisition system for use in a disposable absorbent article arranged to be worn by a wearer to trap and collect fluid waste products of the wearer, the article comprising a top sheet, a fluid absorbent core, a back sheet, said top sheet being arranged to be disposed over said core, said core having a top surface arranged to be located adjacent said top sheet and a bottom surface arranged to be adjacent said back sheet, said method comprising:

(A) providing a layer of a non-woven material having marginal edge portions, each of said marginal edge portions being hydrophillic; and (B) wrapping said core with said layer of said non-woven material so that said marginal edge portions overlap each other over said upper surface of said core, whereupon said overlapping hydrophillic marginal edge portions form a dual layer fluid acquisition system wherein each of said overlapping portions of said non-woven material extends the length of said core.

55. The method of claim 54 comprising:

(C) providing an additional layer of material to form a portion of said fluid acquisition system, said additional layer being located adjacent said overlapping marginal edge portions of said layer of non-woven material and being of a lesser length than the core.

56. The method of claim 55 wherein said additional layer is selected from the group consisting of a non-woven material and a three-dimensional apertured film.

57. The method of claim 56 wherein said additional layer is located between said overlapping marginal edge portions.

58. The method of claim 56 wherein said additional layer is located on top of said overlapping marginal edge portions.

59. The method of claim 56 wherein said additional layer is located below said overlapping marginal edge portions.

* * * * *